(12) United States Patent
Ju

(10) Patent No.: US 11,826,067 B2
(45) Date of Patent: Nov. 28, 2023

(54) MEDICAL SHAVER

(71) Applicant: IMEDICOM CO., LTD., Gunpo-si (KR)

(72) Inventor: Don Soo Ju, Gunpo-si (KR)

(73) Assignee: IMEDICOM CO., LTD., Gunpo-si (KR)

( * ) Notice: Subject to any disclaimer, the term of this patent is extended or adjusted under 35 U.S.C. 154(b) by 493 days.

(21) Appl. No.: 17/258,380

(22) PCT Filed: Jul. 11, 2019

(86) PCT No.: PCT/KR2019/008536
§ 371 (c)(1),
(2) Date: Jan. 6, 2021

(87) PCT Pub. No.: WO2020/022673
PCT Pub. Date: Jan. 30, 2020

(65) Prior Publication Data
US 2021/0282798 A1    Sep. 16, 2021

(30) Foreign Application Priority Data

Jul. 23, 2018    (KR) .......................... 10-2018-0085374

(51) Int. Cl.
*A61B 17/32*    (2006.01)
*A61B 17/00*    (2006.01)
(Continued)

(52) U.S. Cl.
CPC .......... *A61B 17/32* (2013.01); *A61B 17/1659* (2013.01); *A61B 17/32002* (2013.01);
(Continued)

(58) Field of Classification Search
CPC .......... A61B 17/32002; A61B 17/1659; A61B 17/1671; A61B 17/1631; A61B 17/3207;
(Continued)

(56) References Cited

U.S. PATENT DOCUMENTS

| 5,922,003 A * | 7/1999 | Anctil | A61B 17/32002 464/181 |
| 6,979,332 B2 * | 12/2005 | Adams | A61B 17/32002 606/49 |

(Continued)

FOREIGN PATENT DOCUMENTS

| KR | 10-2011-0121715 A | 11/2011 |
| KR | 10-1155437 B1 | 6/2012 |
| KR | 10-2015-0120199 A | 10/2015 |

*Primary Examiner* — Marcela I. Shirsat
(74) *Attorney, Agent, or Firm* — Rabin & Berdo, P.C.

(57) ABSTRACT

The present disclosure provides a medical shaver including: a shaver body (10) having a hollow portion therein; a shaft (20) having one end rotatably attached inside the shaver body and having a motor attachment part provided on the other end that is exposed outside the shaver body; a suction tube (30) rotatably attached to the hollow portion of the shaver body and having one end detachably coupled to the shaft so as to be rotated together with the shaft; a first seating groove (27) provided on an inner circumferential surface of the shaft; a second seating groove (33) provided on an outer circumferential surface of the suction tube; and a spring (s) located in the first and second seating grooves and coupling the shaft and the suction tube, in which the spring (s) has a structure in which both ends of a coil spring are connected to form a ring shape.

4 Claims, 7 Drawing Sheets

(51) Int. Cl.
*A61M 1/00* (2006.01)
*A61B 17/16* (2006.01)
*A61B 17/3207* (2006.01)

(52) U.S. Cl.
CPC ... *A61B 17/3207* (2013.01); *A61B 17/320708* (2013.01); *A61B 2017/0046* (2013.01); *A61B 2017/00398* (2013.01); *A61B 2017/00477* (2013.01); *A61B 2017/320004* (2013.01); *A61B 2217/005* (2013.01); *A61M 1/86* (2021.05)

(58) Field of Classification Search
CPC ...... A61B 17/32078; A61B 17/320708; A61B 2017/320004; A61B 2017/320008; A61B 2017/00398; A61B 2017/0046; A61B 2017/00477; A61B 2017/00261; A61B 2017/320028; A61B 2017/320024; A61B 2017/320733; A61B 2217/005; A61B 1/04; A61M 1/86; A61M 1/00; A61M 1/76
USPC .... 606/79–85, 167, 170, 171, 176, 177, 180
See application file for complete search history.

(56) References Cited

U.S. PATENT DOCUMENTS

| | | | |
|---|---|---|---|
| 2002/0038122 A1* | 3/2002 | Peters | A61B 18/1485 606/45 |
| 2006/0217751 A1* | 9/2006 | O'Quinn | A61B 17/320783 606/180 |
| 2011/0270256 A1* | 11/2011 | Nelson | A61B 17/1659 606/85 |
| 2019/0038305 A1* | 2/2019 | Smith | A61B 90/39 |

* cited by examiner

MEDICAL SHAVER

TECHNICAL FIELD

The present disclosure relates to a medical shaver attached to and used on a medical handpiece and the like, and specifically, to a medical shaver as a tool that is used when discharging decomposed materials such as scraped bone fragments, human tissues, and pus produced during a surgery and the like to the outside, in which the medical shaver is configured such that it is capable of rapid intaking by suction and discharging, and still more specifically, the present disclosure relates to a technology for detachably attaching a part where suctioning is performed.

BACKGROUND ART

Various tools are attached to a front of a handpiece that includes a driving means provided therein, and used as surgical instruments in the course of a medical procedure such as a surgery and the like so as to discharge tissue fragments, scraped tissues, or pus produced during the surgery to the outside. For example, in orthopedics, a suction tip is attached to the front and a saline solution supply tube is formed on one side, such that during a procedure such as a surgery, saline solution is sprayed onto an affected area for cleaning and securing visibility, while the sprayed saline solution and blood spilled during the procedure are suctioned and discharged.

The related technology includes a medical handpiece disclosed in Korean Patent Laid-Open No. 10-2015-0120199. However, the related technology has shortcomings. That is, the parts involved in suctioning are integrally formed and it is inconvenient to attach and detach the parts. Therefore, there is a need to improve a structure of the shaver that is attached to the handpiece or the like, to have a structure that is convenient to use.

SUMMARY

Technical Problem

An object of the present disclosure is to improve a structure of a shaver that is attached to a handpiece, to thus provide a removable suction part and make it easier to attach and detach the suction part.

Technical Solution

The present disclosure provides a medical shaver including: a shaver body 10 having a hollow portion therein; a shaft 20 having one end rotatably attached inside the shaver body and having a motor attachment part provided on the other end that is exposed outside the shaver body; a suction tube 30 rotatably attached to the hollow portion of the shaver body and having one end detachably coupled to the shaft so as to be rotated together with the shaft; a first seating groove 27 provided on an inner circumferential surface of the shaft; a second seating groove 33 provided on an outer circumferential surface of the suction tube; and a spring (s) located in the first and second seating grooves and coupling the shaft and the suction tube, in which the spring (s) has a structure in which both ends of a coil spring are connected to form a ring shape.

The suction tube 30 includes a coupling part detachably coupled to the shaft, and the coupling part includes a docking part 32 having a cross section that is in polygonal shape and thus coupled to a polygonal structure formed on an inner circumferential surface of the shaft when the suction tube is attached.

The coupling part includes: a first coupling part 31-1 formed at a rear end of the docking part and having a circular cross section; a second coupling part 31-2 having a larger diameter than that of the first coupling part and having a circular cross section in which the second seating groove 33 is formed on an outer circumferential surface; and an inclined portion 31s formed between the first coupling part and the second coupling part.

There are two first seating grooves 27, two second seating grooves 33, and two springs S provided, respectively, in which, in the process of attaching the suction tube to the shaft, the springs undergo compression deformation in turn, but in the process of detaching the suction tube from the shaft, the springs undergo deformation at the same time, such that a detaching force for detaching the suction tube from the shaft is greater than an attaching force for attaching the suction tube to the shaft.

The suction tube 30 includes an inner hollow portion, and a suction hole 35 is formed at one end of the hollow portion, and the other end of the hollow portion is connected to an inner hollow portion of the shaft.

Advantageous Effects

By the above configuration, the present disclosure improves the structure of the shaver such that the suction tube is detachably attached to the shaft and a greater force is required for separating and detaching than for attaching the same, and as a result, the suction tube is prevented from being detached while the shaver is in rotating operation, and the procedure is performed more stably.

DETAILED DESCRIPTION

Figure 1:
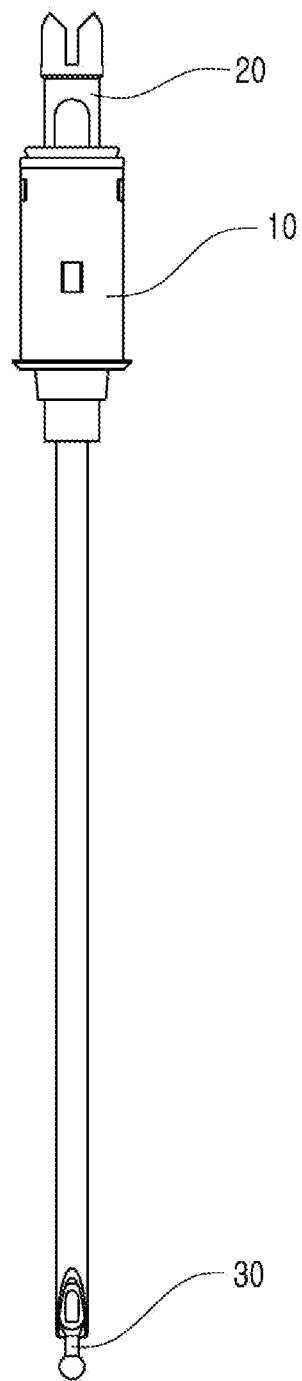
FIG. 1 illustrates a medical shaver according to an embodiment of the present disclosure.
Figure 2:
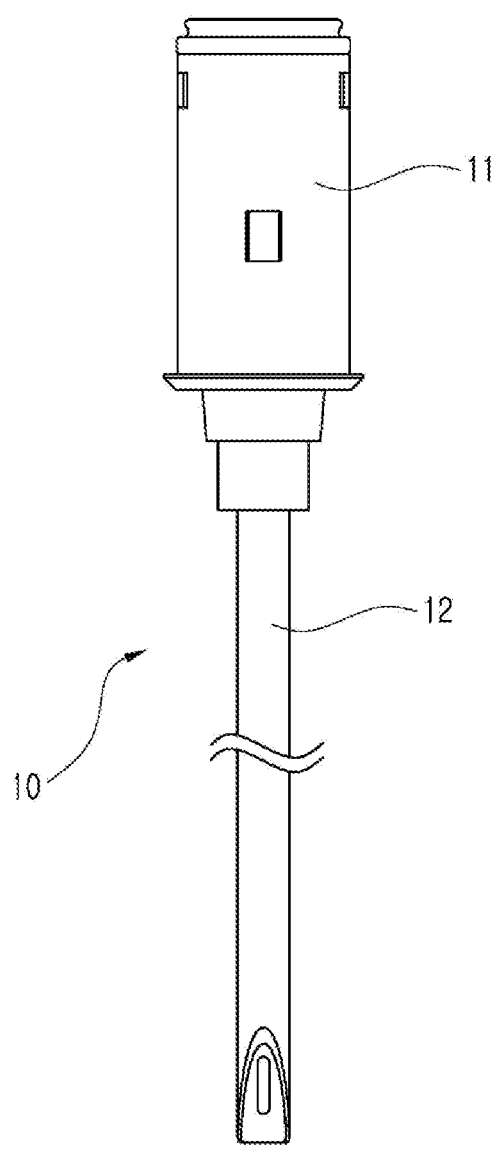
FIG. 2 illustrates only a shaver body and a shaft among the parts of the medical shaver according to an embodiment of the present disclosure.
Figure 3:
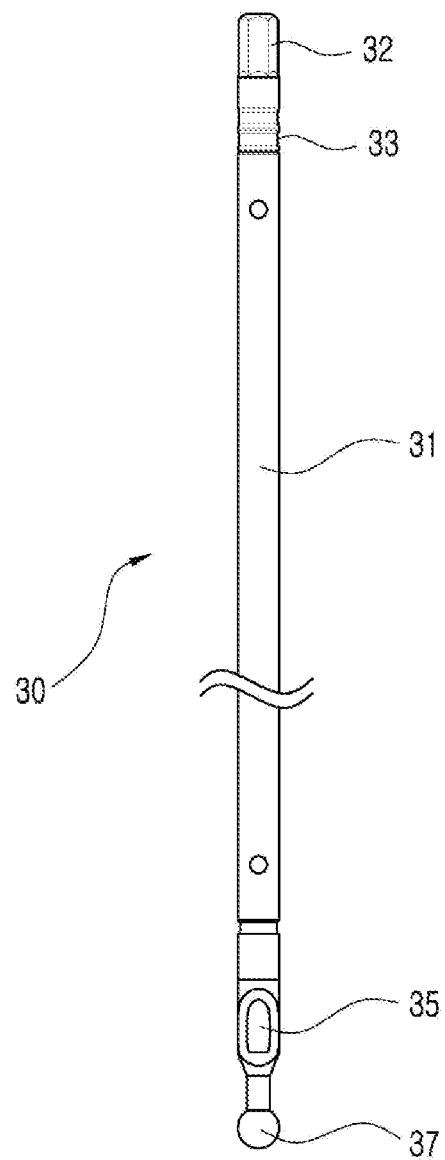
FIG. 3 is a cross-sectional view of FIG. 2.
Figure 4:
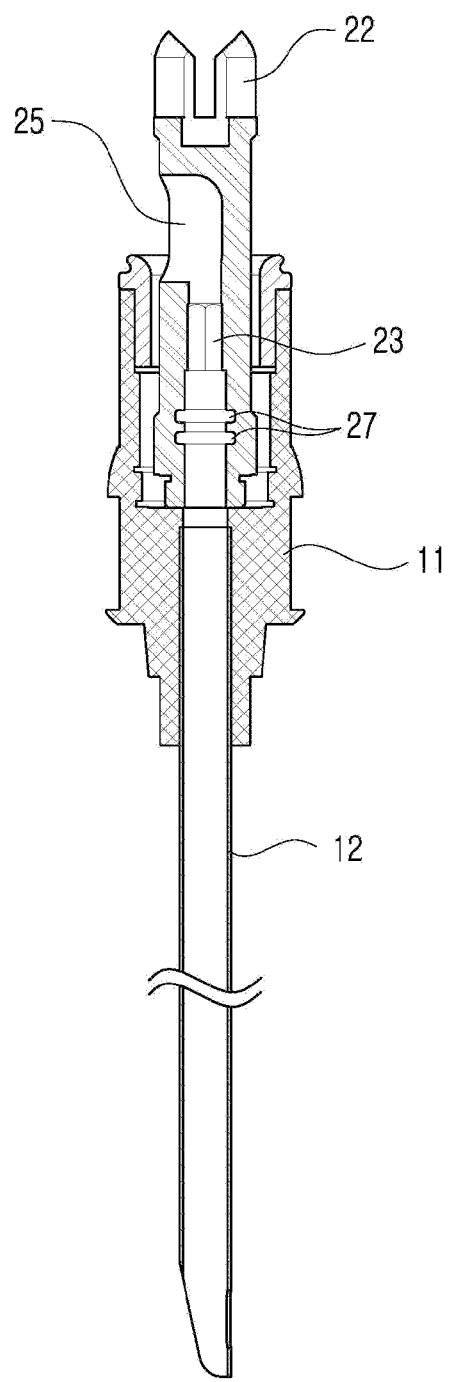
FIG. 4 illustrates a suction tube among the parts of the medical shaver according to an embodiment of the present disclosure.

FIG. 1 illustrates a medical shaver according to an embodiment of the present disclosure. FIG. 2 illustrates only a shaver body and a shaft, FIG. 3 is a cross-sectional view of FIG. 2, FIG. 4 illustrates a suction tube, and FIGS. 5 to 8 are cross-sectional views illustrating a process in which the suction tube and the shaft are coupled and separated in the medical shaver of the present disclosure.

According to the present disclosure, by referring to the drawings, the shaver of the present disclosure includes a shaver body 10 having a longitudinal hollow portion therein, and a shaft 20 and a suction tube 30 having one ends rotatably attached inside the shaver body. The shaft 20 and the suction tube 30, which are attached to the shaver body, are coupled to be rotated together. The shaver of the present disclosure is coupled to a rotation power generating device such as a medical handpiece (not shown), and has a motor coupling part 22 protruding from one side of a body 21 of the shaft 20 to be coupled to the rotation power generating device (motor, etc., not shown). As the shaft is rotated, the suction tube 30 coupled to the shaft is also rotated integrally.

The suction tube 30 has a shape of a tube having a hollow portion therein, and includes, formed at one end thereof, a docking part 32 coupled to a polygonal structure formed on an inner circumferential surface of the shaft. That is, the inner circumferential surface of the shaft has a polygonal (square, hexagonal) cross-sectional structure, and an outer circumferential surface of the docking part 32 has a corresponding polygonal structure, so that the docking part of the suction tube 30 is coupled to the shaft to be rotated integrally.

Figure 5:
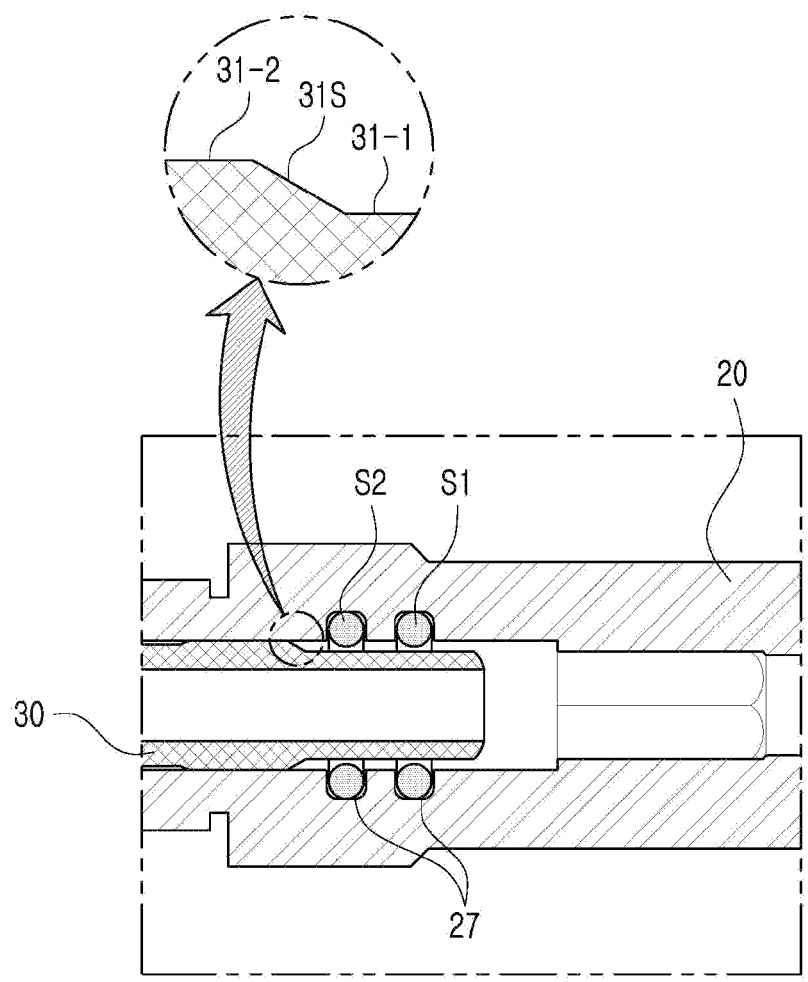
FIGS. 5 to 8 are cross-sectional views illustrating a process in which the suction tube and the shaft are coupled and separated in the medical shaver of the present disclosure.

When a portion of the suction tube that is coupled to the shaft is referred to as a coupling part, the coupling part has a first coupling part 31-1 formed at a rear end of the docking part and having a circular cross section, and a second coupling part 31-2 having a larger diameter than the first coupling part, having a second seating groove 33 formed on an outer circumferential surface, and having a circular cross section, and includes an inclined portion 31s formed between the first coupling part and the second coupling part (see FIG. 5).

In addition, the entire interior of the suction tube 30 has a hollow portion, and there is a suction hole 35 formed at one end of the hollow portion to serve as a suction port through which bone or tissue (hereinafter, discharged matter) is sucked and discharged to the outside as they are scraped during surgery. The discharged matter is sucked into the suction hole 35 and discharged into the hollow portion within the shaft through the hollow portion within the suction tube 30. In addition, the discharged matter is discharged to an external device (medical handpiece, and the like) through a discharge port 25 formed on one side of the shaft. The discharged matter is discharged by a vacuum pressure or the like acting on the discharge port as the shaft is rotated, which is the known technology commonly used in this field, and accordingly, a detailed description thereof will be omitted. The processing part 37 provided on a side of the suction hole of the suction tube is a part that performs an operation such as scraping tissues, or the like during surgery, and may have various shapes such as cutting type.

Figure 9:
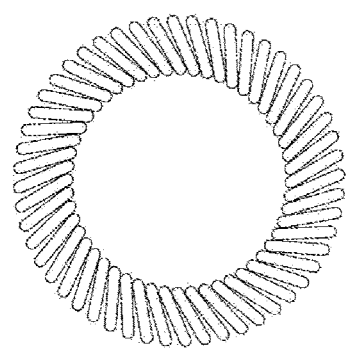
FIG. 9 illustrates a shape of a spring used in the medical shaver of the present disclosure.

Further, a first seating groove 27 for receiving a spring (s) seated therein is provided on the inner circumferential surface of the shaft, and a second seating groove 33 for receiving a spring (s) seated therein is provided on the outer circumferential surface of the suction tube. The spring (s) has a structure in which both ends of a coil spring are connected to form a ring shape as a whole (see FIG. 9), and the springs (s) are located in the first and second seating grooves and serve to couple the shaft and the suction tube to each other so that the shaft and the suction tube do not fall out from each other.

The present disclosure is designed such that, compared to a force required for attaching the suction tube to the shaft, a greater force is required for separating and detaching the same due to the structure of the springs (s) and the first and second seating grooves, and as a result, when the shaver is rotated, the separation of the suction tube is prevented and the procedure is performed more stably. Hereinafter, the process in which the suction tube and the shaft are coupled in the shaver and separated therefrom will be described with reference to the cross-sectional views shown in FIGS. 5 to 8.

The suction tube 30 has a coupling part to be coupled to the shaft, which includes a first coupling part 31-1 formed at a rear end of the docking part 32 and having a circular cross section, a second coupling part 31-2 having a larger diameter than that of the first coupling part, having a circular cross section, and having the second seating groove 33 formed on the outer circumferential surface, and an inclined portion 31s formed between the first coupling part and the second coupling part. Hereinafter, for convenience of explanation, it is assumed that there are two first seating grooves 27, two second seating grooves 33, and two springs (s) provided, respectively, although three or more of each may also be provided. Hereinafter, the springs are referred to as a first spring (s1) and a second spring (s2).

FIG. 5 shows a state in which the suction tube 30 is fitted in the hollow portion of the shaver body and coupled with the shaft 20, and the spring (s) is seated in the first seating groove 27 formed on the inner circumferential surface of the shaft 20, and in this case, the spring is in an extended state (non-compressed state) in the absence of separate force exerted thereon.

Figure 6:
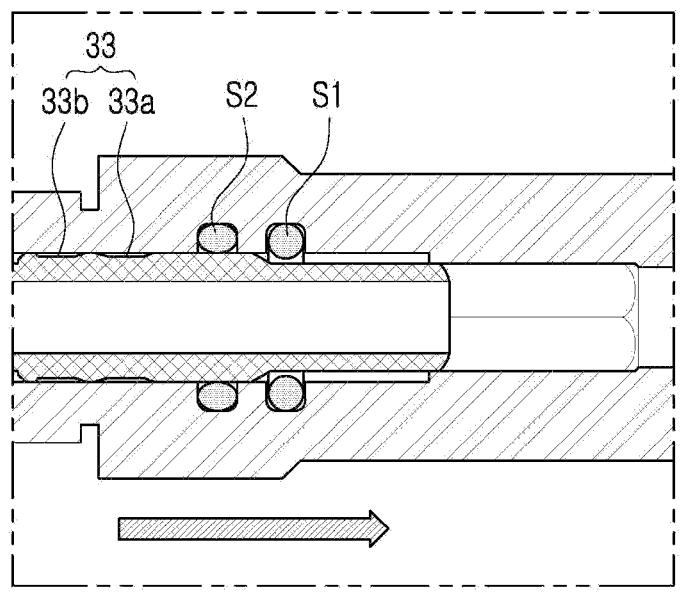

FIG. 6 shows a state in which the suction tube 30 is advanced for coupling, the second spring (s2) is located in the second coupling part 31-2 having a relatively large diameter, and the first spring (s1) is located in the first coupling part 31-1 having a relatively small diameter. That is, with the application of the coupling force, the second spring is moved along the inclined portion 31s into the compressed state, and the first spring is just before the compression.

Figure 7:
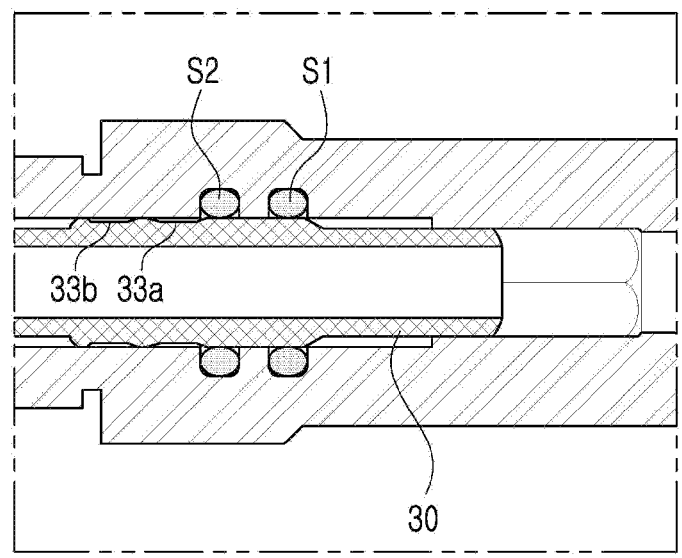
Figure 8:
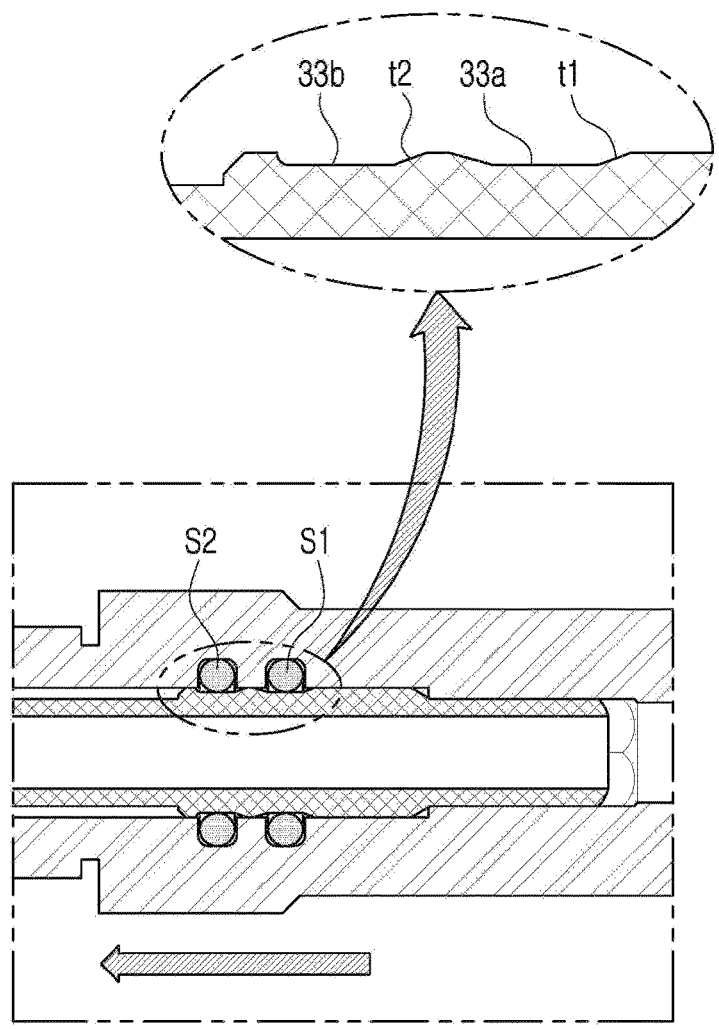

FIG. 7 shows a state in which both the first and second springs are compressed, the suction tube 30 is in the process of continuously advancing (to the right-hand side in the drawing) for coupling, and FIG. 8 shows a state in which the coupling of the suction tube 30 and the shaft 20 is completed, and each of the springs (s1, s2) is seated in the second seating groove 33 formed on the outer circumferential surface of the suction tube. There are two second seating grooves 33, as there are two springs 33a and 33b.

Through the process of FIGS. 5 to 8, the suction tube 30 and the shaft 20 are coupled. Meanwhile, the coupling in this coupling process requires the application of an external force in order to compress the spring when the spring (s) passes through the inclined portion 31s of the suction tube 30 (the friction force when sliding on the outer circumference of the suction tube in the compressed state is insignificant). However, referring to the coupling process, the two springs are compressed one by one, so the force required for compression is a relatively small force.

Consider the case where the suction tube 30 is separated from the shaft 20. In the coupled state shown in FIG. 8, the two springs (s1, s2) are seated in the second seating grooves 33a and 33b, respectively, at which state the springs are not compressed. In order to separate the suction tube 30, it is necessary to pull the suction tube 30 to the left-hand side in the drawing, and at this time, since the two springs (s1, s2) need to be compressed simultaneously to move over the steps (t1 and t2) of the second seating groove, the force required for detachment of the suction tube 30 is roughly about twice the force required for coupling.

Since the structure described above requires that both of the two special springs be contracted at the same time during detachment, it is required that a greater force is applied than the force that is required during coupling. That is, while the springs undergo compression deformation in turn in the process of attaching the suction tube to the shaft, the springs undergo deformation at the same time in the process of detaching the suction tube from the shaft, which means that the detaching force for detaching the suction tube from the shaft is greater than the attaching force for attaching the suction tube to the shaft.

By requiring a greater force for the detachment through this principle, the present disclosure prevents the detachment of the suction tube during the rotation of the shaver, thereby generating an effect of ensuring that the procedure is performed more stably.

What is claimed is:

1. A medical shaver comprising:
    a shaver body (10) having a hollow portion therein;
        a shaft (20) having one end rotatably attached inside the shaver body and having a motor attachment part provided on another end that is exposed outside the shaver body;
        a suction tube (30) rotatably attached to the hollow portion of the shaver body and having one end detachably coupled to the shaft so as to be rotated together with the shaft;
        a first seating groove (27) provided on an inner circumferential surface of the shaft;
        a second seating groove (33) provided on an outer circumferential surface of the suction tube; and
    a spring (s) located in the first and second seating grooves and coupling the shaft and the suction tube, wherein the spring (s) has a structure in which ends of the spring are connected to form a ring shape, wherein the suction tube (30) includes a coupling part detachably coupled to the shaft, and
        the coupling part includes a docking part (32) having a cross section having a polygonal shape and thus coupled to a polygonal structure formed on an inner circumferential surface of the shaft when the suction tube is attached.

2. The medical shaver of claim 1, wherein the coupling part includes:
    a first coupling part (31-1) formed at a rear end of the docking part and having a circular cross section;
    a second coupling part (31-2) having a larger diameter than the first coupling part, and having a circular cross section, wherein the second seating groove (33) is formed on the second coupling part (31-2); and
    an inclined portion (31s) formed between the first coupling part and the second coupling part.

3. The medical shaver of claim 2, including two first seating grooves (27), two second seating grooves (33), and two springs (s), respectively,
    wherein, in a process of attaching the suction tube to the shaft, the springs undergo compression deformation in turn, but
    in a process of detaching the suction tube from the shaft, the springs undergo deformation at a same time such that
    a detaching force for detaching the suction tube from the shaft is greater than an attaching force for attaching the suction tube on the shaft.

4. The medical shaver of claim 1, wherein the suction tube (30) includes an inner hollow portion, and a suction hole (35) is formed at one end of the hollow portion, and another end of the hollow portion is connected to an inner hollow portion of the shaft.

* * * * *